United States Patent [19]

van den Berg et al.

[11] Patent Number: 5,453,214

[45] Date of Patent: Sep. 26, 1995

[54] SUSPENSION AND AGGLOMERATION OF AMIDOPEROXYACIDS

[75] Inventors: Rolf H. van den Berg, Kring van Dorth; Richard H. J. Hekkert, Deventer, both of Netherlands

[73] Assignee: Akzo Nobel N.V., Arnhem, Netherlands

[21] Appl. No.: 211,533

[22] PCT Filed: Sep. 21, 1992

[86] PCT No.: PCT/EP92/02176

§ 371 Date: Jun. 1, 1994

§ 102(e) Date: Jun. 1, 1994

[87] PCT Pub. No.: WO93/07120

PCT Pub. Date: Apr. 15, 1993

[30] Foreign Application Priority Data

Oct. 4, 1991 [EP] European Pat. Off. .............. 91202594

[51] Int. Cl.$^6$ .................. C11D 3/32; C11D 3/395; C11D 11/00; C11D 17/08
[52] U.S. Cl. .................. 252/102; 252/173; 252/174.17; 252/174.23; 252/186.26; 252/186.42; 252/DIG. 14; 264/117; 264/118
[58] Field of Search .................. 252/102, 173, 252/186.26, 186.42, DIG. 14; 264/117, 118

[56] References Cited

U.S. PATENT DOCUMENTS

| | | | |
|---|---|---|---|
| 4,179,394 | 12/1979 | Dillenburg | 252/186 |
| 4,634,551 | 1/1987 | Burns et al. | 252/102 |
| 4,686,063 | 8/1987 | Burns et al. | 252/102 |
| 4,818,425 | 4/1989 | Meijer | 252/94 |
| 4,909,953 | 3/1990 | Sadlowski et al. | 252/99 |
| 5,030,381 | 7/1991 | Zimmermann | 252/186.26 |
| 5,055,218 | 10/1991 | Getty | 252/94 |
| 5,126,066 | 6/1992 | Torenbeek et al. | 252/95 |
| 5,314,639 | 5/1994 | Torenbeek | 252/186.23 |

FOREIGN PATENT DOCUMENTS

| | | | |
|---|---|---|---|
| 0160342 | 11/1985 | European Pat. Off. | 3/395 |
| 0176124 | 4/1986 | European Pat. Off. | 3/39 |
| 0201958 | 11/1986 | European Pat. Off. | 3/395 |
| 0254331 | 1/1988 | European Pat. Off. | 3/39 |
| 0267175 | 5/1988 | European Pat. Off. | 179/22 |
| 0435379 | 7/1991 | European Pat. Off. | 3/39 |
| 1387167 | 3/1975 | United Kingdom | D04H/3/02 |

OTHER PUBLICATIONS

Research Disclosure No. 193, May, 1980, abstract 19302.
International Search Report dated Sep. 21, 1992.

*Primary Examiner*—Dennis Albrecht
*Attorney, Agent, or Firm*—Ralph J. Mancini; Louis A. Morris

[57] ABSTRACT

A process for the suspension agglomeration of amidoperoxyacids which leads to improved rheological storage stability of aqueous suspensions made from these agglomerated peroxyacids is disclosed. Also disclosed are aqueous suspensions of stable viscosity made by milling these agglomerates to a mean particle size of about 20 to about 75 microns.

9 Claims, No Drawings

SUSPENSION AND AGGLOMERATION OF AMIDOPEROXYACIDS

TECHNICAL FIELD

The present invention relates to a process for agglomeration of amidoperoxyacids which leads to improved rheological properties of suspensions made from these agglomerated peroxyacids. The invention further relates to agglomerates made using this process, as well as a process for making suspensions which embodies the agglomeration process and to suspensions made from these agglomerates.

BACKGROUND OF THE INVENTION

Organic peroxyacids are useful as fabric bleaching agents. As such, they are often formulated in the form of either dry, granular compositions, or aqueous suspensions, either of which products can be used in combination with detergent compositions.

An agglomeration process is known for diperoxydodecanedioic acid from published European Patent application number 0 254 331 wherein a water-impermeable material is employed as the agglomeration agent. These agglomerates are made in aqueous suspension at a temperature above the melting point of the water-impermeable material but below the melting and decomposition temperatures of the peroxyacid.

However, this process suffers from the disadvantage that you must employ a significant amount of a water-impermeable material as a binder material in order to make such agglomerates. Use of a water-impermeable material in making bleaching agents is not always possible or desirable.

Amidoperoxyacids made in accordance with EP 0 349 220 have been successfully suspended in aqueous suspensions but, after short storage periods they were found to be rheologically unstable. More particularly, the amidoperoxyacid underwent a change which led to a significant, undesirable viscosity increase. Since liquid bleaching compositions must remain pourable throughput their useful life. Products which thicken to the point of no longer being readily pourable are not commercially acceptable.

Methods for suspending some peroxyacids are known from published European Patent application number 0 347 988, published European Patent application number 0 435 379, published European Patent application number 0 176 124, published European Patent application 0 160 342 and published European patent application number 0 201 958, among others. However, none of these publications teaches or suggests a method of preparing a suspension of the present amidoperoxyacids which do not undergo a significant viscosity increase upon storage.

Accordingly, there exists a need in the art for rheologically stable suspensions of amidoperoxyacids, as well as a method for making such rheologically stable suspensions without negatively affecting one or more of the other properties of the bleaching materials and without the need for significant quantities of water-impermeable materials.

SUMMARY OF THE INVENTION

The present invention relates to a process for the suspension agglomeration of amidoperoxyacids represented by the formulas I and II:

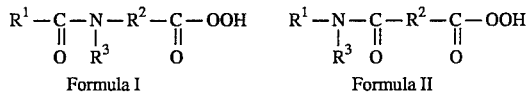

wherein R, is selected from $C_{1-14}$ alk(en)yl, ar(en)yl and alkar(en)yl, $R^2$ is selected from alkyl (ene), aryl(ene) and alkaryl (ene) groups containing from about 1–14 carbon atoms, and $R^3$ is hydrogen or an alkyl, aryl or an aralkyl group containing from about 1 to about 10 carbon atoms; comprising the steps of:

A. preparing an aqueous suspension having a pH of from 2–6 of a composition comprising at least one of said amidoperoxyacids, B. agglomerating said aqueous suspension of peroxyacid at a temperature 0–20° C. below the melting point of said peroxyacid composition, and C. cooling said agglomerated peroxyacid composition to a temperature below 30° C.

The present invention also relates to amidoperoxyacid agglomerates made by this process, a process for making suspensions which employs the aforementioned agglomeration process and to suspensions made from agglomerates which are produced in accordance with the above-described process.

It has surprisingly been found that the agglomeration of amidoperoxyacids at elevated temperature leads to an agglomerate which lends itself to the making of theologically stable suspensions in aqueous suspension systems. More particularly, suspensions made with agglomerates that are produced at elevated temperature remain pourable throughout an acceptable storage period, when compared with the prior art suspensions of the same types of peroxyacid materials.

The invention and its further advantages will be explained in greater detail in the description which follows.

DETAILED DESCRIPTION OF THE INVENTION

Peroxyacids are synthesized, suspended in an aqueous suspension at a pH of from 2–6 and agglomerated. The agglomerated peroxyacid can then be used as a bleaching agent either alone or in combination with a detergent composition.

The present invention applies to amidoperoxyacids.

The amidoperoxyacids can be represented by the formulas I and II:

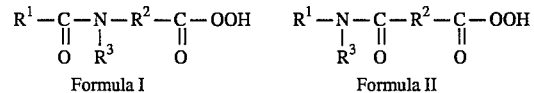

wherein $R^1$ is selected from $C_{1-14}$ alk(en)yl, ar(en)yl, and alkar(en)yl, $R^2$ is selected from alkyl (ene), aryl (ene) and alkaryl(ene) groups containing from about 1–14 carbon atoms, and $R^3$ is hydrogen or an alkyl, aryl or an aralkyl group containing from about 1 to about 10 carbon atoms. These amidoperoxyacids and methods for making them are described in U.S. Pat. Nos. 4,634,551 and 4,686,063, both of which are hereby incorporated by reference.

Preferred amidoperoxyacids are those having the following formula III:

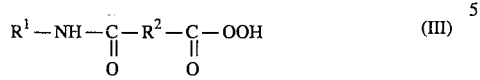
$$R^1-NH-\underset{\underset{O}{\|}}{C}-R^2-\underset{\underset{O}{\|}}{C}-OOH \qquad (III)$$

wherein $R^1$ is an alkyl group containing from 6–12 carbon atoms and R2 is an alkylene group containing 1–6 carbon atoms. The most preferred amidoperoxacids are 4-nonylamido-4-oxoperoxybutanoic acid and 6-nonyl amido-6-oxoperoxyhexanoic acid.

At the end of the typical peroxyacid synthesis the reaction is quenched with water, the products are filtered, washed with water to remove excess acid and filtered again. The peroxyacid wet cake thus obtained may be further processed in accordance with the process of the present invention in order to form either agglomerates of the peroxyacid or suspensions thereof.

The first step in the process of the present invention is to prepare the aqueous suspension media. Aqueous suspension media is set at a pH of between 2 and 6 by addition of an appropriate amount of pH adjusting agent such as an acid or base. The exact pH to be employed will depend to some extent on the particular peroxyacid to be agglomerated. For example, with the preferred amidoperoxyacids a preferred pH is 4.0–5.5 with pH 4.5 being the most preferred when agglomerating an amidoperoxyacid of the formula III.

The aqueous suspension media, in which the agglomeration is carried out, may also contain one or more optional ingredients including buffering agents, exotherm control agents and chelating agents, for example.

In another preferred embodiment of the invention the aqueous suspension media contains a phosphate buffer which is preferably orthophosphate or pyrophosphate in a concentration range of from 0.01 molar to 1.0 molar. Most preferred is a 0.10 molar solution of orthophosphates. These can be selected from the group of phosphoric acid, monobasic sodium phosphate, dibasic sodium phosphate and tribasic sodium phosphate. The final solution must have a pH between 2 and 6, and more preferably between 4 and 5.5. The pH of the buffered solution can be adjusted to the appropriate range by addition of sodium hydroxide, for example. Of course, other cations such as potassium may be employed in the buffering agent.

Chelants may also optionally be incorporated in the aqueous suspension media. Examples of suitable chelants for use herein are carboxylates, such as ethylene diamine tetraacetate (EDTA) and diethylene triamine pentaacetate (DTPA); polyphosphates, such as sodium acid pyrophosphate (SAPP), tetrasodium pyrophosphate (TSPP) and sodium tripolyphosphate (STPP); phosphonates, such as ethylhydroxydiphosphonate (Dequest® 2010) and other sequestering agents sold under the Dequest® tradename; dipicolinic acid, picolinic acid, citric acid and 8-hydroxyquinoline; and combinations of the above.

Preferably 0.01–10% of such chelants are employed. More preferably, 0.1–5.0% of chelant is employed. All amounts in this patent application are percentage by weight; based on the total weight of the particular composition in question, unless otherwise specified.

The peroxyacid composition is preferably suspended prior to agglomeration in the form of a wet cake which is fresh from the synthesis process. A typical composition will contain 30–60% by weight of peroxyacid, 35–65% by weight water and the balance organic impurities which comprise mainly unreacted starting materials from the synthesis process.

The peroxyacid wet cake is mixed into the aqueous suspension media by a suitable mixing or agitating apparatus. For example, a double-armed turbine stirrer can be used for this mixing.

The peroxyacid may be added to the aqueous suspension media at any temperature below the decomposition temperature of the peroxyacid such as room temperature, but, in a preferred embodiment, the aqueous suspension media is first warmed to a temperature which is 0–20° C. below the melting point of the peroxyacid composition. Then, the peroxyacid is added thereto. In this manner, decomposition of the peroxyacid, which may occur at elevated temperatures, is kept to a minimum. Most preferably, the aqueous suspension media is 5–15° C. below the melting point of the peroxyacid composition when the peroxyacid is added.

Since the suspension media is aqueous, this places a limitation of 100° C. on the agglomeration temperature. However, peroxyacid compositions having a higher melting point can still be agglomerated by the present process. More particularly, a material can be added to the aqueous suspension media which does not adversely affect the peroxyacid or the agglomeration process and effectively elevates the boiling point of the suspension media. Certain salts and glycols could be employed.

Another alternative is to employ one or more fatty alcohols, fatty acids or fatty esters as diluents in the peroxyacid composition whereby the melting point of the peroxyacid composition can be depressed below 100° C. A particularly suitable material is lauric acid.

After addition of the peroxyacid composition to the aqueous suspension media, if necessary, the pH is returned to 2–6 by further addition of the appropriate agent, in this case normally sodium hydroxide.

Once the peroxyacid composition has been added to the aqueous suspension media, the suspension is warmed to an agglomeration temperature of 0–20° C. below the melting point of the peroxyacid composition to thereby agglomerate said peroxyacid composition into agglomerates of the desired size. The agglomeration is continued until the agglomerates are the size which is desired.

Agglomeration occurs as a result of the partial melting of the peroxyacid composition which then agglomerates with itself. Agglomeration normally occurs in a short time period of about 20–60 minutes, depending upon how close the agglomeration temperature is to the melting point of the peroxyacid composition. The desired size of the agglomerates is generally from 200 to 2000 μm, although other sizes are also possible.

Once the agglomerates are of the desired size, the agglomerated material is cooled to below 30° C. This cooling step is preferably a rapid cooling to minimize peroxyacid decomposition and to prevent further buildup of the agglomerates beyond the desired size. The agglomerates may then by separated by filtration.

The agglomerates generally comprise the peroxyacid, some stabilizer, some organic impurities and the balance water. A typical agglomerate will contain 30–70% by weight of peroxyacid, and perhaps more if the agglomerate is subjected to drying.

The agglomerates produced by the present process are physically different than agglomerates produced at an agglomeration temperature of 20–30° C., for example. It is this physical difference which makes it possible to stably suspend these agglomerates in a liquid bleaching agent suspension which remains rheologically stable over long storage periods. For example, when compared to suspensions made directly from peroxyacid wet cake, the present suspensions do not exhibit the undesirable viscosity increase which is observed in the case where the peroxyacid was suspended without a prior agglomeration step. Accordingly, the agglomerates are an improvement over existing agglomerates of these peroxyacids.

In another embodiment of the present invention, the peroxyacid agglomerates are further processed into stable, bleaching suspensions, either in the same vessel in which they were agglomerated, or in a two-step process.

In particular, the suspension may be made by adding sufficient water to the agglomerates to act as the suspension media and then adding from 0.1 to 1.0 weight percent, based on said suspension, xanthan gum and 0.02 to 2.0 weight percent, based on said suspension, of a second polymer selected from polyvinyl alcohol, one or more cellulose derivatives, and mixtures thereof. The suspension is most preferably made under high shear conditions, such as with an Ultra-Turrax® stirring apparatus.

Aqueous surfactant structured liquids are also capable of suspending the present peroxyacid agglomerates without the need of a thickening agent and can be obtained by using a single surfactant or mixtures of surfactants in combination with an electrolyte.

The preparation of surfactant-based suspending liquids normally requires a nonionic and/or an anionic surfactant and an electrolyte, though other types of surfactant or surfactant mixtures, such as the cationics and zwitterionics, can also be used. Indeed, various surfactants or surfactant pairs or mixtures can be used in combination with several different electrolytes, but it should be appreciated that electrolytes which would readily be oxidised by peroxy acids, such as chlorides, bromides and iodides, and those which are not compatible with the desired acid pH range, e.g. carbonates and bicarbonates, should preferably be excluded from the peroxy acid suspending surfactant liquid compositions of the invention.

Examples of different surfactant/electrolyte combinations suitable for preparing the peroxy acid suspending surfactant structured liquids are:

a) surfacants:
  (i) coconut diethanolamide/alkylbenzene sulphonate;
  (ii) $C_9$–$C_{16}$ alcohol ethoxylate/alkylbenzene sulphonate;
  (iii) lauryl ethersulphate/alkylbenzene sulphonate;
  (iv) alcohol ether sulphate;
  in combination with:
b) electrolytes:
  (i) sodium sulphate and/or
  (ii) sodium nitrate.

Accordingly, another suspension in accordance with the invention encompasses aqueous liquid bleaching compositions comprising an effective amount of a solid, particulate, substantially water-insoluble amido peroxyacid stably suspended in an aqueous liquid containing a surfactant and an electrolyte, said compositions having an acid pH in the range of from 2 to 6, preferably from 4 to 5.5.

This suspension of the invention may contain from about 1 to 40% by weight of the peroxy acid, preferably from 2.5 to about 30% by weight.

As explained, the surfactants usable in this embodiment can be anionic, nonionic, cationic, zwitterionic or soap in nature or mixtures thereof.

The anionics comprise the well-known anionic surfactants of the alkyl aryl sulphonate type, the alkyl sulphate and alkyl ether sulphate types, the alkane and alkene sulphonate type etc. In these surfactants the alkyl radicals may contain from 9–20 carbon atoms. Numerous examples of such materials can be found in Schwartz, Perry, Vol. II, 1958, "Detergents and Surface Active Agents".

Specific examples of suitable anionic surfactants include sodium lauryl sulphate, potassium dodecyl sulphonate, sodium dodecyl benzene sulphonate, sodium salt of lauryl polyoxyethylene sulphate, dioctyl ester of sodium sulphosuccinic acid and sodium lauryl sulphonate.

The nonionics comprise ethylene oxide and/or propylene oxide condensation products with alcohols, alkylphenol, fatty acids and fatty acid amides. These products generally contain 5 to 30 ethylene oxide and/or propylene oxide groups. Fatty acid mono- and dialkylolamides, as well as tertiary amine oxides are also included in the terminology of nonionic detergent-active materials.

Specific examples of nonionic detergents include nonyl phenol polyoxyethylene ether, tridecyl alcohol polyoxyethylene ether, dodecyl mercaptan polyoxyethylene thioether, the lauric ester of polyethylene glycol, $C_{12}$–$C_{15}$ primary alcohol/7 ethylene oxide, the lauric ester of sorbitan polyoxyethylene ether, tertiary alkyl amine oxide and mixtures thereof.

Other examples of nonionic surfactants can be found in Schwartz, Perry, Vol. II, 1958, "Detergents and Surface Active Agents" and Schick, Vol. I, 1967, "Nonionic Surfactants".

The cationic detergents which can be used in the present invention include quaternary ammonium salts which contain at least one alkyl group having from 12 to 20 carbon atoms. Although the halide ions are the preferred anions, other suitable anions include acetate, phosphate, sulphate, nitrite, and the like.

Specific cationic detergents include distearyl dimethyl ammonium chloride, stearyl dimethyl benzyl ammonium chloride, stearyl trimethyl ammonium chloride, coco dimethyl benzyl ammonium chloride, dicoco dimethyl ammonium chloride, cetyl pyridinium chloride, cetyl trimethyl ammonium bromide, stearyl amine salts that are soluble in water such as stearyl amine acetate and stearyl amine hydrochloride, stearyl dimethyl amine hydrochloride, distearyl amine hydrochloride, alkyl phenoxyethoxyethyl dimethyl ammonium chloride, decyl pyridinium bromide, pyridinium chloride derivative of the acetyl amino ethyl esters of lauric acid, lauryl trimethyl ammonium chloride, decyl amine acetate, lauryl dimethyl ethyl ammonium chloride, the lactic acid and citric acid and other acid salts of stearyl-1-amido-imidazoline with methyl chloride, benzyl chloride, chloroacetic acid and similar compounds, mixtures of the foregoing, and the like.

Zwitterionic detergents include alkyl-β-iminodipropionate, alkyl-β-aminopropionate, fatty imidazolines, betaines, and mixtures thereof.

Specific examples of such detergents are 1-coco-5-hydroxyethyl-5-carboxymethyl imidazoline, dodecyl-β-alanine, the inner salt of 2-trimethyl amino lauric acid, and N-dodecyl-N,N-dimethyl amino acetic acid.

The total surfactant amount in the liquid bleaching suspension of the invention may vary from 2 to 50% by weight, preferably from 5 to 35% by weight, depending on the purpose of use. In the case of suspending liquids comprising an anionic and anonionic surfactant the ratio thereof may vary from about 10:1 to 1:10. The term anionic surfactant used in this context includes the alkali metal soaps of synthetic or natural long-chain fatty acids having normally from 12 to 20 carbon atoms in the chain.

The total level of electrolyte(s) present in the composition to provide structuring may vary from about 1.5 to about 30%, preferably from 2.5 to 254 by weight.

When suspending the agglomerates of the present invention it is important to mill the agglomerated peroxyacid composition so that the majority of the particles are less than 150 μm in diameter. A preferred particle size range is from 1–150 μm with a mean particle size in the area of 20–75 μm.

The resultant suspensions are also physically different from prior art suspensions of the same peroxyacids, as shown by their extended rheological stability which is demonstrated in the examples appended hereto. These suspensions can be used as liquid bleaching compositions either alone, in combination with powdered detergents as a two component system, or in combination with liquid detergents either as a two-component system or as a one-component system wherein the detergent and bleaching composition are combined into one liquid.

The bleaching compositions of the present invention have been found to have the same level of activity as the prior art suspensions, the same level of chemical stability and a much higher level of rheological stability.

The present invention will be further exemplified by the examples which follow. These examples are not to be interpreted as limiting the invention in any way and the scope of the invention is to be determined from the claims appended hereto.

EXAMPLE 1

A 2 liter aqueous buffer solution containing 5% by weight of monobasic sodium phosphate and 1% by weight of Dequest® 2010 was adjusted to a pH of 4.5 with a solution of sodium hydroxide. The buffer solution was warmed to 60° C. with stirring at about 400 rotations per minute. Once the buffer solution reached 60° C., 600 grams of 6-nonylamido-6-oxoperoxyhexanoic acid wet cake containing 35% by weight of 6-nonylamido-6-oxoperoxyhexanoic acid, 4% by weight of organic impurities and the balance water, was added with continued stirring. The pH was again adjusted to 4.5. Heating was continued until the agglomerates were of the desired size (at about 69° C.) at which point the agglomerates were rapidly cooled to less than 30° C. The agglomerates were then separated from the water with a glass filter. A yield of 300 grams of agglomerates containing about 62% by weight of 6-nonylamido-6-oxoperoxyhexanoic acid was obtained.

The agglomerates were then used to prepare a bleach suspension with the following composition:
10.2% 6-nonylamido-6-oxoperoxyhexanoic acid (calculated on pure, dry peroxyacid),
0.25% dipicolinic acid,
1.0% polyvinyl alcohol,
0.5% xanthan gum, and the balance water.

The suspension was prepared by first mixing the polyvinyl alcohol, xanthan gum, dipicolinic acid and water with a turbine stirrer for one hour. Next, the peroxyacid agglomerates were admixed and the pH was adjusted to 4.5 with a sodium hydroxide solution. The suspension was finely milled with an Ultra Turrax® $T_{50}$ rotor-stator dissolver to a mean particle size of 33 μm and a maximum particle size of approximately 150 μm.

The viscosity of the suspension was 34 mPa's at a shear rate of 200 s$^{-1}$. After 4 weeks storage at 40° C. the viscosity was 77 mPa's. The suspension remained pourable for the entire storage period.

Comparative Example A

Starting with the same peroxyacid wet cake as was used for the agglomeration step of Example 1, a suspension was prepared in accordance with Example 1 except that the peroxyacid wet cake was not agglomerated. A suspension with a mean particle size of 13 μm and an approximate maximum particle size of 100 μm was obtained. This suspension was pourable having an initial viscosity of 32 mPa's. After 1 week storage at 40° C. a gel structure had formed and the suspension was no longer pourable. After stirring a viscosity of 350 mPa's was measured, but upon further storage at 40° C the gel structure reformed.

EXAMPLE 2

In the same manner as Example 1, peroxyacid wet cake was agglomerated. The agglomerates were then used to prepare a suspension using 1 auryl alkyl sulphonate and sodium toluene sulphonate as the suspending agents. A thin, pourable suspension was obtained with a mean particle size of 23 μm and an approximate maximum particle size of 130 μm. The viscosity was found to be 10 mPa's. After 1 week storage at 40° C. the viscosity was 78 mPa's and the suspension remained pourable. After two weeks storage at 40° C. the viscosity was 72 mPa's and the suspension remained pourable.

Comparative Example B

The procedure of Example 2 was repeated except that peroxyacid wet cake was used to prepare the suspension, without first agglomerating it. The suspension was thin and pourable having a mean particle size of 13 μm and an approximate maximum particle size of 67 pro. The viscosity of the suspension was 19 mPa's. After 1 week storage at 40° C. a gel had formed and the suspension was no longer pourable. After stirring the viscosity was measured at 250 mPa's. After an additional week of storage at 40° C. the gel structure had returned and the viscosity after stirring was measured at 380 mPa's.

EXAMPLE 3

To 600 ml demineralized water 3.2 g dipicolinic acid was added and the pH was adjusted to 3.0 with a solution of sodium hydroxide. 595 grams of 4-nonylamido-4-oxoperoxybutanoic acid wet cake containing 34.4% by weight of peroxyacid, 3.5% by weight of organic impurities, and the balance water, was added with stirring at about 400 rotations per minute. The pH was again adjusted to 3.0.

The mixture was heated under continuous stirring until agglomerates were obtained of the desired size (at about 63° C.). Next the mixture was cooled to below 30° C. and a bleach suspension was prepared by adding 12.6 grams polyvinyl alcohol and 2.5 grams xanthan gum, mixing for one hour and finally milling the suspension with and Ultra Turrax® T50 rotor-stator dissolver to a mean particle size of 28 μm and a maximum particle size of approximately 150 μm.

The composition of this suspension was:
16.2% 4-nonylamido-4-oxoperoxybutanoic acid (calculated on pure, dry peroxyacid),
0.25% dipicolinic acid,
1.0% polyvinyl alcohol,
0.2% xanthum gum, and the balance water.

The viscosity of the suspension was 48 mPa.s at a shear rate of 200 s$^{-1}$. After two weeks storage at 40° C. the viscosity was 130 mPa.s and after 4 weeks it was 165 mPa.s. It remained pourable.

Comparative Example C

Starting with the same 4-nonylamido-4-oxoperoxybutanoic acid wet cake as was used for the agglomeration step of example 3 a suspension was prepared with the same composition as in example 3, except that the peroxyacid was not agglomerated. A suspension with a mean particle size of 9 μm and a maximum particle size of 43 μm was obtained. This suspension had an initial viscosity of 45 mPa.s but after I week storage at 40° C. a gel structure had formed and the suspension was no longer pourable. After stirring a viscosity of 770 mPa.s was found. Upon further storage at 40° C. the gel structure returned.

EXAMPLE 4

A suspension was prepared starting with peroxyacid agglomerates as described in Example 1 using the following composition:

10.04 6-nonylamido-6-oxoperoxyhexanoic acid (calculated on pure, dry peroxyacid),
6.34 Sodium alkyl benzene sulphonate,
2.74 $C_{12}$–$C_{15}$ primary alcohol/ethylene oxide,
6.34 anhydrous sodium sulphate, and balance water + NaOH for pH adjusted to 4.5.

The suspension was finely milled with an Ultra Turrax rotor-stator dissolver to a mean particle size of 29 μm and a maximum particle size of approximately 76 μm.

The viscosity of the suspension was 265 mPa.s at a shear rate of 200 s$^{-1}$, after one week storage at 40° C. the viscosity was 365 mPa.s and after two weeks at 40° C. the viscosity was 540 mPa.s. It remained pourable for the entire storage period.

Comparative Example D

A suspension was prepared with the same composition as in Example 4 but starting with the peroxyacid wet cake without prior agglomeration. A suspension with a mean particle size of 19 μm and a maximum particle size of 105 pm was obtained.

The initial viscosity of this suspension was 385 mPa.s. After 1 week storage a gel structure had formed and it was no longer pourable.

The gel structure was broken by stirring and a viscosity of 600 mPa.s was measured.

After 2 weeks storage the gel structure had returned. It was broken by stirring and a viscosity of 660 mPa.s was found.

What is claimed is:

1. A process for preparing rheologically stable suspensions of suspension agglomerated amidoperoxyacid which remain pourable throughout acceptable storage periods wherein said amidoperoxyacids are represented by the formulas I and II:

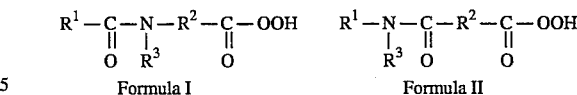

Formula I      Formula II wherein $R^1$ is selected from $C_{1-16}$ alk(en)yl, ar(en)yl and alkar(en)yl, $R^2$ is selected from alky(ene), aryl(ene) and alkaryl(ene) groups containing from about 1–14 carbon atoms, and $R^3$ is hydrogen or an alkyl, aryl or an aralkyl group containing from about 1 to about 10 carbon atoms; and wherein said process comprises:

A. preparing an aqueous suspension having a pH of from 2–6 of a composition comprising at least one of said amidoperoxyacids, B. agitating said aqueous suspension of peroxyacid of step A at a temperature 0–20° C. below the melting point of said peroxyacid composition for a time sufficient to form agglomerates having a particle size of 200–2000 μm;

C. milling the agglomerates to a mean particle size of form about 20 to about 75 μm;

D. cooling said agglomerated peroxyacid composition to a temperature below 30° C.; and E. suspending the agglomerated peroxyacid in an aqueous media in order to form a suspension having from about 1–40% by weight peroxyacid.

2. The process of claim 1 wherein step A comprises preparing an aqueous suspension media having a pH of from 2–6, heating said aqueous suspension media to a temperature 0–20° C. below the melting temperature of the peroxyacid and adding said peroxyacid to said heated aqueous suspension media.

3. The process of claim 1 wherein said peroxyacid is selected from 4-nonylamido-4-oxoperoxybutanoic acid and 6-nonylamido-6oxoperoxyhexanoic acid.

4. The process of claim 1 wherein step A further comprises contacting said peroxyacid with a buffer solution.

5. The process of claim 1 wherein said aqueous suspension media in which said peroxyacid composition is agglomerated, comprises 0.01–10 weight percent of a chelating agent.

6. The process of claim 1 wherein step D comprises suspending the agglomerated peroxyacid in an aqueous medium comprising 0.1 to 1.0 weight percent, based on said suspension, of xanthan gum and 0.02 to 2.0 weight percent, based on said suspension, of a second polymer selected from polyvinyl alcohol, one or more cellulose derivatives, and mixtures thereof.

7. The process of claim 1 wherein step D comprises suspending the agglomerated peroxyacid in an aqueous medium containing 2–50 weight percent of a surfactant and 1.5 to 30 weight percent of an electrolyte.

8. A liquid peroxyacid bleaching composition which comprises the suspension of claim 1.

9. A detergent composition comprising the liquid peroxyacid bleaching composition of claim 8.

* * * * *